United States Patent
Auler et al.

(10) Patent No.: US 6,844,294 B2
(45) Date of Patent: Jan. 18, 2005

(54) SYNERGISTIC HERBICIDAL COMPOSITIONS COMPRISING HERBICIDES FROM THE BENZOYLCYCLOHEXANEDIONE GROUP FOR USE IN RICE CROPS

(75) Inventors: Thomas Auler, Bad Soden (DE); Andreas van Almsick, Karben (DE); Erwin Hacker, Hochheim (DE); Jean-Claude Millet, Ecully (FR); Keiji Endo, Akeno-machi (JP)

(73) Assignee: Aventis CropScience GmbH, Frankfurt am Main ( * ) Notice: Subject to any disclaimer, the term of this patent is extended or adjusted under 35 U.S.C. 154(b) by 0 days.

(21) Appl. No.: 10/126,147

(22) Filed: Apr. 18, 2002

(65) Prior Publication Data

US 2003/0104941 A1 Jun. 5, 2003

(30) Foreign Application Priority Data

Apr. 21, 2001 (DE) ......................................... 101 19 727

(51) Int. Cl.[7] ........................ A01N 43/80; A01N 41/10; A01N 35/06
(52) U.S. Cl. ........................ 504/134; 504/136; 504/138; 504/271; 504/292; 504/294; 504/333; 504/348
(58) Field of Search ................................. 504/271, 134, 504/136, 138, 292, 294, 333, 248, 127, 221, 225

(56) References Cited

U.S. PATENT DOCUMENTS 6,376,429 B1 * 4/2002 Van Almsick et al. ...... 504/271
6,573,218 B1 * 6/2003 Tsukamoto et al. ......... 504/221
6,576,593 B2 * 6/2003 van Almsick et al. ...... 504/134

FOREIGN PATENT DOCUMENTS

| DE | 42 16 880 A1 | 11/1993 |
|---|---|---|
| EP | 0 949 257 | 10/1999 |
| WO | WO 91/05469 | 5/1991 |
| WO | WO 96/15673 | 5/1996 |
| WO | WO 96/32013 | 10/1996 |
| WO | WO 97/48275 | 12/1997 |
| WO | WO 97/48276 | 12/1997 |
| WO | WO 98/29406 | 7/1998 |
| WO | WO 00/03591 | 1/2000 |
| WO | WO 00/21924 | 4/2000 |
| WO | WO 00/30447 | 6/2000 |
| WO | WO 01/07422 | 2/2001 |
| WO | WO 01/28341 A2 | 4/2001 |

OTHER PUBLICATIONS

Database WPI, Accession No. 1997–292214; also referred to as XP 002214682.

* cited by examiner

Primary Examiner—Sabiha Qazi
(74) Attorney, Agent, or Firm—Frommer Lawrence & Haug LLP

(57) ABSTRACT

Described are herbicidal compositions comprising

A) at least one compound from the benzoylcyclohexanedione group and

B) at least one compound from the group of the herbicides which act selectively against monocotyledonous and/or dicotyledonous harmful plants in rice.

These compositions have a superior action compared with the herbicides employed individually.

6 Claims, No Drawings

SYNERGISTIC HERBICIDAL COMPOSITIONS COMPRISING HERBICIDES FROM THE BENZOYLCYCLOHEXANEDIONE GROUP FOR USE IN RICE CROPS

The invention relates to the technical field of the crop protection products which can be employed against undesired vegetation and which comprise, as active ingredients, a combination of at least two herbicides.

More specifically, it relates to herbicidal compositions for use in rice which comprise, as active ingredient, a herbicide from the benzoylcyclohexanedione group in combination with at least one further herbicide.

Herbicides from the abovementioned benzoylcyclohexanedione group are known from a large number of documents. Thus, for example, the herbicidal action of a large number of such compounds is described in WO 98/29406, WO 00/21924 and WO 01/07422. Some of the benzoylcyclohexanediones mentioned in WO 00/21924 have a good herbicidal action against harmful plants which grow in rice crops.

In practice, however, the use of the benzoylcyclohexanediones known from these publications frequently entails disadvantages. Thus, the herbicidal activity is not always sufficient, or, if the herbicidal activity is sufficient, undesired damage to the rice plants is observed.

The activity of herbicides depends, inter alia, on the type of the herbicide employed, its application rate, the preparation, the harmful plants to be controlled, the climatic conditions and soil conditions and the like. Another criterion is the duration of action or degradation rate of the herbicide. Where appropriate, changes in the sensitivity of harmful plants to an active ingredient, which may occur upon prolonged use or within a geographically defined area, may also have to be taken into account. Such changes manifest themselves as more or less pronounced losses of action and can only be compensated for to a certain extent by increasing the application rates of the herbicides.

Owing to the large number of possible influencing factors, there exists virtually no single active ingredient which combines the desired properties for the various uses, in particular with regard to the species of the harmful plants and the climatic zones. What is more, there are constant demands for achieving the effect with increasingly smaller herbicide rates. A lesser rate reduces not only the amount of an active ingredient required for application, but also, as a rule, the amount of formulation auxiliaries required. Both reduce the financial input and improve the eco-friendliness of the herbicide treatment.

A method which is frequently used for improving the use characteristics of a herbicide is to combine the active ingredient with one or more other active ingredients which contribute the desired additional properties. However, phenomena of physical and biological incompatibility are frequently observed when several active ingredients are used as a combination, for example lack of stability of a coformulation, degradation of an active ingredient, or antagonism of the active ingredients. In contrast, combinations of active ingredients with an advantageous spectrum of action, high stability and the highest possible synergistically enhanced action, which allows the application rate to be reduced in comparison with the individual application of the active ingredients to be combined, are desired.

Herbicidal mixtures of 2-(4-methylsulfonyl-2-nitrobenzoyl)-1,3-cyclohexanedione with a sulfonylurea from the group consisting of nicosulfuron, rimsulfuron, thifensulfuron-methyl, primisulfuron-methyl, prosulfuron and halosulfuron are disclosed in WO 97/48275. However, these mixtures are not suitable for use in rice crops since they also inflict considerable damage on the rice plants.

It is an object of the present invention to provide herbicidal compositions for use in rice crops, which compositions have improved properties compared with the prior art.

The invention relates to herbicidal compositions comprising an effective content of A) at least one compound of the formula (I) and agriculturally customary salts thereof [component (A)]

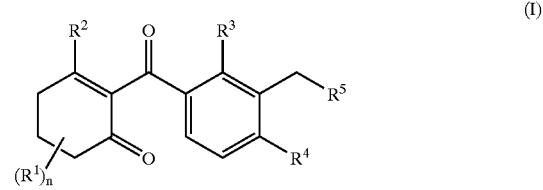

(I)

where
$R^1$ is $C_1$–$C_4$-alkyl;
$R^2$ is $OR^6$, $SO_mR^7$, cyanato, cyano, thiocyanato or halogen;
$R^3$ and $R^4$ independently of one another are hydrogen, halogen, $C_1$–$C_4$-alkyl, halogen-$C_1$–$C_4$-alkyl, cyano, nitro or $SO_mR^7$;
$R^5$ is O—$(CH_2)_a$—O—$(CH_2)_b$—$OR^7$, $C_3$–$C_8$-cycloalkyloxy, $C_3$–$C_8$-cycloalkyl-$C_1$–$C_4$-alkyloxy, 2-tetrahydrofuranylmethoxy, 3-tetrahydrofuranylmethoxy, 2-tetrahydro-2H-pyranylmethoxy, 2-tetrahydrothienylmethoxy, 2-furanylmethoxy or 2-thienylmethoxy;
$R^6$ is hydrogen, $C_1$–$C_4$-alkyl or halogen-$C_1$–$C_4$-alkyl;
$R^7$ is $C_1$–$C_4$-alkyl, $C_2$–$C_4$-alkenyl, $C_2$–$C_4$-alkynyl, halogen-$C_1$–$C_4$-alkyl, halogen-$C_2$–$C_4$-alkenyl or halogen-$C_2$–$C_4$-alkynyl;
n is 0, 1, 2, 3, 4, 5 or 6;
m is 0, 1 or 2;
a is 2, 3 or 4;
b is 2, 3 or 4; and B) at least one compound [component (B)] from the group consisting of the herbicides benfuresate (B1.1), bensulfuron (B2.1), bispyribac-sodium (B2.2), clomazone (B3.1), cyhalofop-butyl (B4.1), ethoxysulfuron (B2.3), fenoxaprop-ethyl (B4.2), foramsulfuron (B2.4), glufosinate (B10.1), glyphosate (B11.1), halosulfuron-methyl (B2.5), imazamox (B2.6), imazapyr (B2.7), imazaquin (B2.8), imazethapyr (B2.9), imazosulfuron (B2.10), iodosulfuron-methyl-sodium (B2.11), mefenacet (B5.1), mesosulfuron (B2.12), metosulam (B2.13), metsulfuron-methyl (B2.14), oxadiargyl (B6.1), oxaziclomefone (B5.2), pentoxazone (B6.2), pendimethalin (B7.1), propanil (B8.1), quinclorac (9.1) and thiobencarb (B1.2), these compositions comprising the compounds of the formula (I) or salts thereof [component (A)] and the compounds of the group B) [component (B)] in a weight ratio of 1:200 to 200:1.

Preferred compositions comprise the compounds of the formula (I) or salts thereof [component (A)] and the compounds of group B) [component (B)] in a weight ratio of 1:20 to 20:1.

In formula (I) and all the subsequent formulae, chain-like carbon-containing radicals such as alkyl, alkoxy, haloalkyl, haloalkoxy, alkylamino and alkylthio and the corresponding unsaturated radicals and/or radicals which are substituted in the carbon skeleton, such as alkenyl and alkynyl, can in each case be straight-chain or branched. Alkyl radicals, also in the composite meanings such as alkoxy, haloalkyl and the like, are, for example, methyl, ethyl, n- or i-propyl, n-, i-, t- or 2-butyl. Alkenyl and alkynyl radicals have the meanings of the possible unsaturated radicals which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-in-1-yl, but-3-in-1-yl, 1-methylbut-3-in-1-yl. The multiple bond can be located in any desired position of the unsaturated radical.

Cycloalkyl is a carbocyclic saturated ring system, for example cyclopropyl, cyclopentyl or cyclohexyl.

Halogen is fluorine, chlorine, bromine or iodine. Haloalkyl and haloalkenyl are alkyl, alkenyl or alkynyl, each of which is partially or fully substituted by halogen, preferably by fluorine, chlorine and/or bromine, in particular by fluorine and/or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this also applies analogously to haloalkenyl.

Depending on the type and the linkage of the substituents, the compounds of the formula I may exist as stereoisomers. If, for example, one or more alkenyl groups are present, diastereomers may occur. If, for example, one or more asymmetric carbon atoms are present, enantiomers and diastereomers may occur. Stereoisomers can be obtained from the mixtures obtained in the preparation by customary separation methods, for example by chromatographic separation methods. Equally, stereoisomers may be prepared selectively by using stereoselective reactions and optically active starting materials and/or auxiliaries. The invention also relates to all stereoisomers and their mixtures which are encompassed by the formula I, but not defined specifically.

Preferred herbicidal compositions comprise, as component (A), a compound of the formula (I) where $R^1$ is methyl;

$R^2$ is $OR^6$;

$R^3$ and $R^4$ independently of one another are hydrogen, chlorine, fluorine, methyl, trifluoromethyl, cyano, nitro or $SO_2R^7$;

$R^6$ is hydrogen;

$R^7$ is methyl or ethyl;

n is 0, 1 or 2;

m, a and b are in each case 2.

Also preferred are herbicidal compositions that comprise, as component (A), a compound of the formula (I), in which $R^5$ is $O—(CH_2)_a—O—(CH_2)_b—OR^7$, $C_3$–$C_8$-cycloalkyloxy, $C_3$–$C_8$-cycloalkyloxy-$C_1$–$C_4$-alkyloxy or 2-tetrahydrofuranylmethoxy.

Furthermore preferred are herbicidal compositions that comprise, as component (A), a compound of the formula (Ia) with the meanings stated hereinbelow:

(Ia)

| No. | $R^3$ | $R^4$ | $R^5$ |
|---|---|---|---|
| (A1) | Cl | $SO_2CH_3$ | (2-tetrahydrofuranylmethoxy) |
| (A2) | Cl | $SO_2CH_3$ | (cyclohexylmethoxy) |
| (A3) | Cl | $SO_2CH_3$ | (cyclopentyloxy) |
| (A4) | Cl | $SO_2CH_3$ | (cyclohexylmethoxy, longer chain) |
| (A5) | Cl | $SO_2CH_3$ | $O(CH_2CH_2O)_2CH_2CH_3$ |
| (A6) | $CF_3$ | $SO_2CH_2CH_3$ | $O(CH_2CH_2O)_2CH_2CH_3$ |
| (A7) | Cl | $SO_2CH_2CH_3$ | (cyclopropyloxy) |
| (A8) | Cl | $SO_2CH_2CH_3$ | (cyclohexyloxy) |
| (A9) | $CF_3$ | $SO_2CH_2CH_3$ | $O(CH_2CH_2O)_2CH_3$ |
| (A10) | $CH_3$ | $SO_2CH_3$ | $O(CH_2CH_2O)_2CH_3$ |
| (A11) | Cl | $SO_2CH_3$ | $O(CH_2CH_2O)_2CH_3$ |
| (A12) | $CH_3$ | $SO_2CH_3$ | $O(CH_2CH_2O)_2CH_2CH_3$ |

The chemical structures of the active ingredients whose common names have been stated hereinabove are known, for example, from "The Pesticide Manual", 12th Edition, 2000, British Crop Protection Council, or can be seen from the table which follows:

| Common name | Structure |
|---|---|
| foramsulfuron | N-[(4,6-dimethoxypyrimidin-2-yl)-aminocarbonyl]-2-dimethyl-aminocarbonyl-5-formylamino-benzenesulfonamide |
| mesosulfuron | N-[(4,6-dimethoxypyrimidin-2-yl)-aminocarbonyl]-2-methoxy-carbonyl-5-methylsulfonylaminomethyl-benzenesulfonamide |

Foramsulfuron is disclosed as a herbicide for example in WO 95/10507.

Mesosulfuron is disclosed as a herbicide for example in WO 95/10507.

Herbicidal compositions which are of particular interest in this context are those with a synergistically active content of one or more of the following combinations of two compounds (A)+(B):

(A1)+(B1.1), (A1)+(B1.2), (A1)+(B2.1), (A1)+(B2.2), (A1)+(B2.3), (A1)+(B2.4), (A1)+(B2.5), (A1)+(B2.6), (A1)+(B2.7), (A1)+(B2.8), (A1)+(B2.9), (A1)+(B2.10), (A1)+(B2.11), (A1)+(B2.12), (A1)+(B2.13), (A1)+(B2.14), (A1)+(B3.1), (A1)+(B4.1), (A1)+(B4.2), (A1)+(B5.1), (A1)+(B5.2), (A1)+(B6.1), (A1)+(B6.2), (A1)+(B7.1), (A1)+(B8.1), (A1)+(B9.1), (A1)+(B10.1), (A1)+(B11.1), (A2)+(B1.1), (A2)+(B1.2), (A2)+(B2.1), (A2)+(B2.2), (A2)+(B2.3), (A2)+(B2.4), (A2)+(B2.5), (A2)+(B2.6), (A2)+(B2.7), (A2)+(B2.8), (A2)+(B2.9), (A2)+(B2.10), (A2)+(B2.11), (A2)+(B2.12), (A2)+(B2.13), (A2)+(B2.14), (A2)+(B3.1), (A2)+(B4.1), (A2)+(B4.2), (A2)+(B5.1), (A2)+(B5.2), (A2)+(B6.1), (A2)+(B6.2), (A2)+(B7.1), (A2)+(B8.1), (A2)+(B9.1), (A2)+(B10.1), (A2)+(B11.1), (A3)+(B1.1), (A3)+(B1.2), (A3)+(B2.1), (A3)+(B2.2), (A3)+(B2.3), (A3)+(B2.4), (A3)+(B2.5), (A3)+(B2.6), (A3)+(B2.7), (A3)+(B2.8), (A3)+(B2.9), (A3)+(B2.10), (A3)+(B2.11), (A3)+(B2.12), (A3)+(B2.13), (A3)+(B2.14), (A3)+(B3.1), (A3)+(B4.1), (A3)+(B4.2), (A3)+(B5.1), (A3)+(B5.2), (A3)+(B6.1), (A3)+(B6.2), (A3)+(B7.1), (A3)+(B8.1), (A3)+(B9.1), (A3)+(B10.1), (A3)+(B11.1), (A4)+(B1.1), (A4)+(B1.2), (A4)+(B2.1), (A4)+(B2.2), (A4)+(B2.3), (A4)+(B2.4), (A4)+(B2.5), (A4)+(B2.6), (A4)+(B2.7), (A4)+(B2.8), (A4)+(B2.9), (A4)+(B2.10), (A4)+(B2.11), (A4)+(B2.12), (A4)+(B2.13), (A4)+(B2.14), (A4)+(B3.1), (A4)+(B4.1), (A4)+(B4.2), (A4)+(B5.1), (A4)+(B5.2), (A4)+(B6.1), (A4)+(B6.2), (A4)+(B7.1), (A4)+(B8.1), (A4)+(B9.1), (A4)+(B10.1), (A4)+(B11.1), (A5)+(B1.1), (A5)+(B1.2), (A5)+(B2.1), (A5)+(B2.2), (A5)+(B2.3), (A5)+(B2.4), (A5)+(B2.5), (A5)+(B2.6), (A5)+(B2.7), (A5)+(B2.8), (A5)+(B2.9), (A5)+(B2.10), (A5)+(B2.11), (A5)+(B2.12), (A5)+(B2.13), (A5)+(B2.14), (A5)+(B3.1), (A5)+(B4.1), (A5)+(B4.2), (A5)+(B5.1), (A5)+(B5.2), (A5)+(B6.1), (A5)+(B6.2), (A5)+(B7.1), (A5)+(B8.1), (A5)+(B9.1), (A5)+(B10.1), (A5)+(B11.1), (A6)+(B1.1), (A6)+(B1.2), (A6)+(B2.1), (A6)+(B2.2), (A6)+(B2.3), (A6)+(B2.4), (A6)+(B2.5), (A6)+(B2.6), (A6)+(B2.7), (A6)+(B2.8), (A6)+(B2.9), (A6)+(B2.10), (A6)+(B2.11), (A6)+(B2.12), (A6)+(B2.13), (A6)+(B2.14), (A6)+(B3.1), (A6)+(B4.1), (A6)+(B4.2), (A6)+(B5.1), (A6)+(B5.2), (A6)+(B6.1), (A6)+(B6.2), (A6)+(B7.1), (A6)+(B8.1), (A6)+(B9.1), (A6)+(B10.1), (A6)+(B11.1), (A7)+(B1.1), (A7)+(B1.2), (A7)+(B2.1), (A7)+(B2.2), (A7)+(B2.3), (A7)+(B2.4), (A7)+(B2.5), (A7)+(B2.6), (A7)+(B2.7), (A7)+(B2.8), (A7)+(B2.9), (A7)+(B2.10), (A7)+(B2.11), (A7)+(B2.12), (A7)+(B2.13), (A7)+(B2.14), (A7)+(B3.1), (A7)+(B4.1), (A7)+(B4.2), (A7)+(B5.1), (A7)+(B5.2), (A7)+(B6.1), (A7)+(B6.2), (A7)+(B7.1), (A7)+(B8.1), (A7)+(B9.1), (A7)+(B10.1), (A7)+(B11.1), (A8)+(B1.1), (A8)+(B1.2), (A8)+(B2.1), (A8)+(B2.2), (A8)+(B2.3), (A8)+(B2.4), (A8)+(B2.5), (A8)+(B2.6), (A8)+(B2.7), (A8)+(B2.8), (A8)+(B2.9), (A8)+(B2.10), (A8)+(B2.11), (A8)+(B2.12), (A8)+(B2.13), (A8)+(B2.14), (A8)+(B3.1), (A8)+(B4.1), (A8)+(B4.2), (A8)+(B5.1), (A8)+(B5.2), (A8)+(B6.1), (A8)+(B6.2), (A8)+(B7.1), (A8)+(B8.1), (A8)+(B9.1), (A8)+(B10.1), (A8)+(B11.1), (A9)+(B1.1), (A9)+(B1.2), (A9)+(B2.1), (A9)+(B2.2), (A9)+(B2.3), (A9)+(B2.4), (A9)+(B2.5), (A9)+(B2.6), (A9)+(B2.7), (A9)+(B2.8), (A9)+(B2.9), (A9)+(B2.10), (A9)+(B2.11), (A9)+(B2.12), (A9)+(B2.13), (A9)+(B2.14), (A9)+(B3.1), (A9)+(B4.1), (A9)+(B4.2), (A9)+(B5.1), (A9)+(B5.2), (A9)+(B6.1), (A9)+(B6.2), (A9)+(B7.1), (A9)+(B8.1), (A9)+(B9.1), (A9)+(B10.1), (A9)+(B11.1), (A10)+(B1.1), (A10)+(B1.2), (A10)+(B2.1), (A10)+(B2.2), (A10)+(B2.3), (A10)+(B2.4), (A10)+(B2.5), (A10)+(B2.6), (A10)+(B2.7), (A10)+(B2.8), (A10)+(B2.9), (A10)+(B2.10), (A10)+(B2.11), (A10)+(B2.12), (A10)+(B2.13), (A10)+(B2.14), (A10)+(B3.1), (A10)+(B4.1), (A10)+(B4.2), (A10)+(B5.1), (A10)+(B5.2), (A10)+(B6.1), (A10)+(B6.2), (A10)+(B7.1), (A10)+(B8.1), (A10)+(B9.1), (A10)+(B10.1), (A10)+(B11.1), (A11)+(B1.1), (A11)+(B1.2), (A11)+(B2.1), (A11)+(B2.2), (A11)+(B2.3), (A11)+(B2.4), (A11)+(B2.5), (A11)+(B2.6), (A11)+(B2.7), (A11)+(B2.8), (A11)+(B2.9), (A11)+(B2.10), (A11)+(B2.11), (A11)+(B2.12), (A11)+(B2.13), (A11)+(B2.14), (A11)+(B3.1), (A11)+(B4.1), (A11)+(B4.2), (A11)+(B5.1), (A11)+(B5.2), (A11)+(B6.1), (A11)+(B6.2), (A11)+(B7.1), (A11)+(B8.1), (A11)+(B9.1), (A11)+(B10.1), (A11)+(B11.1), (A12)+(B1.1), (A12)+(B1.2), (A12)+(B2.1), (A12)+(B2.2), (A12)+(B2.3), (A12)+(B2.4), (A12)+(B2.5), (A12)+(B2.6), (A12)+(B2.7), (A12)+(B2.8), (A12)+(B2.9), (A12)+(B2.10), (A12)+(B2.11), (A12)+(B2.12), (A12)+(B2.13), (A12)+(B2.14), (A12)+(B3.1), (A12)+(B4.1), (A12)+(B4.2), (A12)+(B5.1), (A12)+(B5.2), (A12)+(B6.1), (A12)+(B6.2), (A12)+(B7.1), (A12)+(B8.1), (A12)+(B9.1), (A12)+(B10.1) and (A12)+(B11.1).

With the combinations according to the invention, application rates in the range of from 1 to 2 000 g, preferably 10 to 500 g, of active ingredient component (A) and from 1 to 2 000 g, preferably 1 to 500 g, of component (B) are generally required per hectare (ai/ha).

The weight ratios of components (A) to (B) to be employed can be varied within wide ranges. The quantitative ratio is preferably in the range of from 1:50 to 500:1, in particular in the range of from 1:20 to 50:1. Optimal weight ratios can depend on the field of application in question, the weed spectrum and the active ingredient combination employed and can be determined in preliminary experiments.

The compositions according to the invention are outstandingly suitable for the selective control of harmful plants in rice crops.

The compositions according to the invention can be employed in all those modes of application which are conventional for rice herbicides. They are especially advantageously employed in the form of spray application and submerged application. In what is known as submerged application, the paddy water already has a depth of up to 30 mm above the soil at the point in time of application. The compositions according to the invention are added to the paddy water directly, for example in the form of granules. Worldwide, spray application is employed predominantly in seeded rice and what is known as submerged application predominantly in transplanted rice.

The compositions according to the invention act on a broad weed spectrum. For example, they are suitable for controlling annual and perennial harmful plants such as, for example, from the species *Abutilon, Alopecurus, Avena, Chenopodium, Cynodon, Cyperus, Digitaria, Echinochloa, Elymus, Galium, Ipomoea, Lamium, Matricaria, Scirpus, Setaria, Sorghum, Veronica, Viola* and *Xanthium*, in particular *Echinochloa* spp., *Leptochloa* spp., *Scirpus* spp., *Cyperus* spp., *Sagittaria* spp., *Monochoria* spp., *Lindernia* spp., *Eleocharis* spp. and *Sesbania* spp.

The herbicidal compositions according to the invention are also distinguished by a reduced effective dosage of components (A) and (B) used in the combinations in comparison with individual dosage, so that a reduction in the required active ingredient rates is made possible.

The invention also relates to a method of controlling undesired vegetation, which comprises applying one or more herbicides (A) together with one or more herbicides (B) to the harmful plants, plant parts thereof, or the area under cultivation.

When type (A) and (B) herbicides are applied jointly, superadditive (=synergistic) effects are observed. The action of the combinations exceeds the expected total of the actions of the individual herbicides employed and the action of each individual herbicide (A) ad (B). The synergistic effects allow a reduction in application rate, the control of a broader spectrum of broad-leaved and grass weeds, a more rapid onset of the herbicidal action, a prolonged duration of action, a better control of the harmful plants with only one or few applications, and an extension of the application period which is possible. These properties are required in weed control practice to keep agricultural crops free from undesired competing plants, thus safeguarding and/or increasing the yields in terms of quality and quantity. The technical standard is markedly exceeded by these new combinations with regard to the properties described.

The active ingredient combinations according to the invention can both be present as mixed formulations of components (A) and (B), if appropriate together with further customary formulation auxiliaries, which are then applied in the customary manner in the form of a dilution with water, or can be prepared as what are known as tank mixes, by jointly diluting the components, all or some of which are formulated separately, with water.

Components (A) and (B) can be formulated in various ways, depending on the prevailing biological and/or chemico-physical parameters. The following are suitable as examples of formulations which are generally possible: wettable powders (WP), emulsifiable concentrates (EC), aqueous solutions (SL), emulsions (EW) such as oil-in-water and water-in-oil emulsions, sprayable solutions or emulsions, oil- or water-based dispersions, suspoemulsions, dusts (DP), seed-dressing products, granules for soil application or spreading, water-dispersible granules (WG), ULV formulations, microcapsules or waxes.

The individual types of formulation are known in principle and are described, for example, in: Winnacker-Küchler, "Chemische Technologie" [Chemical Engineering], Volume 7, C. Hauser Verlag Munich, 4th Ed. 1986; van Valkenburg, "Pesticides Formulations", Marcel Dekker N.Y., 1973; K. Martens, "Spray Drying Handbook", 3rd Ed. 1979, G. Goodwin Ltd. London. The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J.; H.v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridegewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976, Winnacker-Küchler, "Chemische Technologie", Volume 7, C. Hauser Verlag Munich, 4th Ed. 1986.

Based on these formulations, combinations with other pesticidally active substances, such as other herbicides, fungicides or insecticides, and with safeners, fertilizers and/or growth regulators, may also be prepared, for example in the form of a readymix or a tank mix.

Wettable powders are products which are uniformly dispersible in water and which, besides the active ingredient, also comprise ionic or nonionic surfactants (wetters, dispersants), for example polyoxethylated alkylphenols, polyethoxylated fatty alcohols or fatty amines, alkanesulfonates, alkylbenzenesulfonates, sodium lignosulfonates, sodium 2,2'-dinaphthylmethane-6,6'-disulfonate, sodium dibutylnaphthalinesulfonate, or else sodium oleoylmethyltauride, in addition to a diluent or inert material.

Emulsifiable concentrates are prepared by dissolving the active ingredient in an organic solvent, for example butanol, cyclohexanone, dimethylformamide, xylene or else higher-boiling aromatics or hydrocarbons with addition of one or more ionic or nonionic surfactants (emulsifiers). Examples of emulsifiers which may be used are: calcium salts of alkylarylsulfonic acids, such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxethylene sorbitol esters.

Dusts are obtained by grinding the active ingredient with finely divided solid materials, for example talc, natural clays such as kaolin, bentonite and pyrophyllite, or diatomaceous earth.

Granules can be prepared either by spraying the active ingredient onto adsorptive granulated inert material or by applying active ingredient concentrates to the surface of carriers such as sand, kaolinites or granulated inert material with the aid of adhesives, for example polyvinyl alcohol, sodium polyacrylate or else mineral oils. Suitable active ingredients may also be granulated in the manner conventionally used for fertilizer granules, if desired in a mixture with fertilizers. As a rule, water-dispersible granules are prepared by processes such as spray drying, fluidized-bed granulation, disk granulation, mixing with high-speed mixers, and extrusion without solid inert material.

The agrochemical formulations comprise, as a rule, from 0.1 to 99 percent by weight, in particular from 0.2 to 95% by weight, of active ingredient types (A) and (B), the following concentrations being customary, depending on the type of formulation: the active ingredient concentration in wettable powders is, for example, from approximately 10 to 95% by weight, the remainder to 100% by weight being composed of customary formulation constituents. In the case of emulsifiable concentrates, the active ingredient concentration may amount to, for example, 5 to 80% by weight. Formulations in the form of dust usually comprise from 5 to 20% by weight of active ingredient, and sprayable solutions comprise approximately from 0.2 to 25% by weight of active ingredient. In the case of granules, such as dispersible granules, the active ingredient content depends partly on whether the active compound is present in liquid or solid form and on which granulation auxiliaries and fillers are being used. As a rule, the active ingredient content amounts to between 10 and 90% by weight in the case of the water-dispersible granules. In addition, the abovementioned active ingredient formulations comprise, if appropriate, the adhesives, wetters, dispersants, emulsifiers, preservatives, antifreeze agents, solvents, fillers, colorants, carriers, antifoams, evaporation inhibitors, pH regulators or viscosity regulators which are customary in each case.

For use, the formulations, which are present in commercially available form, are, if appropriate, diluted in the customary manner, for example using water in the case of wettable powders, emulsifiable concentrates, dispersions and water-dispersible granules. Preparations in the form of dusts, soil granules, granules for spreading, and sprayable solutions, are usually not diluted any further with other inert substances prior to use.

The active ingredients can be applied to the plants, plant parts, plant seeds or the area under cultivation (arable soil), preferably to the green plants and plant parts and, if appropriate, additionally to the arable soil.

One possible use is the joint application of active ingredients in the form of tank mixes, the optimally formulated concentrated formulations of the individual active ingredients jointly being mixed with water in the tank and the spray mixture obtained being applied.

A herbicidal coformulation of the combination according to the invention of components (A) and (B) has the advantage of greater ease on use since the amounts of the components are already presented in the correct proportion. Moreover, the auxiliaries in the formulation can be adjusted to match each other optimally, while a tank mix of different formulations may result in undesired combinations of auxiliaries.

A. FORMULATION EXAMPLES a) A dust (WP) is obtained by mixing 10 parts by weight of an active ingredient/active ingredient mixture and 90 parts by weight of talc as inert substance and comminuting the mixture in a hammer mill.

b) A wettable powder (WG) which is readily dispersible in water is obtained by mixing 25 parts by weight of an active ingredient/active ingredient mixture, 64 parts by weight of kaolin-containing quartz as inert material, 10 parts by weight of potassium lignosulfonate and 1 part by weight of sodium oleoylmethyltauride as wetter and dispersant and grinding the mixture in a pinned-disk mill.

c) A dispersion concentrate which is readily dispersible in water is obtained by mixing 20 parts by weight of an active ingredient/active ingredient mixture with 6 parts by weight of alkylphenyl polyglycol ether (Triton X 207); 3 parts by weight of isotridecanol polyglycol ether (8 EO) and 71 parts by weight of paraffinic mineral oil (boiling range, for example, approx. 255 to 277° C.) and grinding the mixture in a friction bowl mill to a fineness of under 5 microns.

d) An emulsifiable concentrate (EC) is obtained from 15 parts by weight of an active ingredient/active ingredient mixture, 75 parts by weight of cyclohexanone as solvent and 10 parts by weight of oxethylated nonylphenol as emulsifier.

e) Water-dispersible granules are obtained by mixing
75 parts by weight of an active ingredient/active ingredient mixture,
10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill and granulating the powder in a fluidized bed by spraying on water as granulating fluid.

f) Water-dispersible granules are also obtained by homogenizing and pre-comminuting
25 parts by weight of an active ingredient/active ingredient mixture,
5 parts by weight of sodium 2,2'-dinaphthylmethane-6,6'-disulfonate,
2 parts by weight of sodium oleoylmethyltauride,
1 part by weight of polyvinyl alcohol,
17 parts by weight of calcium carbonate and
50 parts by weight of water
in a colloid mill, subsequently grinding the mixture in a bead mill, and atomizing and drying the suspension thus obtained in a spray tower by means of a single-substance nozzle.

B. BIOLOGICAL EXAMPLES

1. Pre-emergence Herbicidal Action

Seeds or root segments of monocotyledonous and dicotyledonous harmful plants are placed in sandy loam in pots and covered with soil. In the case of spray application, the compositions formulated as concentrated aqueous solutions, wettable powders or emulsion concentrates, are then applied to the surface of the covering soil as aqueous solution, suspension or emulsion, respectively, at an application rate of 600 to 800 l of water per ha (converted) in a variety of dosages. Immediately to a few days after the application, the test containers are flooded with water up to a depth of 30 mm above the soil surface. In the case of submerged application, in contrast, the soil in the closed test container is already covered with paddy water up to a depth of 30 mm at the time of application. Here, the formulated active ingredients are added directly to the paddy water, for example in the form of granules. After the treatment, the pots are placed in a greenhouse and kept under good growth conditions for the weeds. Visual scoring of the plant damage or the adverse effect on the emergence is carried out after the test plants have emerged after an experimental period of 3 to 4 weeks in comparison with untreated controls. As demonstrated by the test results, the compositions according to the invention have an outstanding pre-emergence herbicidal action against a broad spectrum of grass weeds and broad-leaved weeds. Frequently, effects of the combinations according to the invention are observed which exceed the formal total of the effects when the herbicides are applied individually. When using suitable low dosages, the values observed in the experiments show an effect of the combinations which exceed the expected values calculated using Colby's formula.

Scoring and Assessing the Synergistic Herbicidal Effects

The herbicidal efficacy of the active ingredients or active ingredient mixtures was scored visually by comparing the treated variants with untreated control variants. The damage and development of all aerial plant parts was recorded. Scoring was done on a percentage scale (100% action=all plants dead; 50% action=50% of the plants and green plant parts dead; 0% action=no discernible action=like untreated control plot).

2. Post-emergence Herbicidal Action

Seeds or root segments of monocotyledonous and dicotyledonous weeds are placed in sandy loam in pots, covered with soil and grown in the greenhouse under good growth conditions (temperature, atmospheric humidity, water supply). Approximately three weeks after planting, the experimental plants are treated with the compositions according to the invention. In the case of spray application, the compositions according to the invention, which are formulated as wettable powders or emulsion concentrates, are sprayed onto the green plant parts in various dosages with an application rate of 600 to 800 l of water per ha (converted). Immediately to a few days after the application, the test containers are flooded with water up to a depth of 30 mm above the soil surface. In the case of submerged application, in contrast, the soil in the closed test container is already covered with paddy water up to a depth of 30 mm at the time of application. Here, the formulated active ingredients are added directly to the paddy water. After the experimental plants have remained in the greenhouse under optimal growth conditions for a further 3 to 4 weeks, the effect of the preparations is scored visually in comparison with untreated controls. The compositions according to the invention also have an outstanding herbicidal action against a broad spectrum of economically important grass weeds and broad-leaved weeds when applied post-emergence. Frequently, effects of the combinations according to the invention are observed which exceed the formal total of the effects when the herbicides are applied individually. When using suitable low dosages, the values observed in the experiments show an effect of the combinations which exceed the expected values calculated using Colby's formula.

3. Herbicidal Action and Crop Plant Tolerance (Field Experiments)

Crop plants were grown in the open on plots under natural field conditions, seeds or root segments of typical harmful plants having been planted and the natural weed flora being exploited. The treatment with the compositions according to the invention was carried out as spray application or submerged application after the harmful plants and the crop plants had emerged, as a rule in the 2- to 4-leaf stage; in some cases (as stated), individual active ingredients or active ingredient combinations were applied pre-emergence or as sequential treatment, partly pre-emergence and/or post-emergence. After the application, for example 2, 4, 6 and 8 weeks after the application, the effect of the preparations is scored visually in comparison with untreated controls (for scoring, see Example 1). The compositions according to the invention also have a synergistic herbicidal activity against a broad spectrum of economically important grass weeds and broad-leaved weeds in field experiments. The comparison demonstrated that the combinations according to the invention have in most cases a more potent, in some cases a considerably more potent, herbicidal action than the total of the actions of the individual herbicides and therefore suggests synergism. Moreover, the effects exceeded the expected values calculated using Colby's formula during important parts of this scoring period, and therefore likewise suggest synergism. The crop plants, in contrast, were left unharmed or virtually unharmed as the consequence of treatment with the herbicidal compositions.

When applying the combinations according to the invention, herbicidal effects are frequently observed on a harmful plant species which exceed the formal total of the effects of the herbicides present when these are applied by themselves. Alternatively, it is observed in some cases that a lower application rate is required for the herbicide combination in order to achieve the same effect on a harmful plant species in comparison with the individual products. Such increases in action or efficacy, or reduced application rates, strongly suggest a synergistic effect. When the data observed already exceed the formal total of the data in the experiments with individual applications, they likewise exceed the expected value calculated by Colby's formula hereinbelow, which is likewise regarded as suggesting synergism (cf. S. R. Colby; in Weeds 15 (1967) pp. 20 to 22):

$$E = A + B - \frac{A \times B}{100}$$

In this formula:
A, B=action of component A or B in percent at a dosage of a and b grams of ai/ha, respectively, and
E=expected value in % at a dosage of a+b grams of ai/ha.

The data observed in the abovementioned experimental examples exceed the expected values calculated using Colby's formula.

SAGPY *Sagittaria pygmaea*
SCPJU *Scirpus juncoides*
SEBEX *Sesbania exaltata*

Example B.I

| Compound | Dosage [g ai/ha] | CYPSE found | value E (according to Colby) | SEBEX found | value E (according to Colby) |
|---|---|---|---|---|---|
| A1 | 10 | 5% | | | |
| | 20 | | | 25% | |
| B2.1 | 10 | 68% | | | |
| | 20 | | | 45% | |
| A1 + B2.1 | 10 + 10 | 88% | 70% | | |
| | 37.5 + 75 | | | 78% | 59% |

Example B.II

| Compound | Dosage [g ai/ha] | PHBPU found | value E (according to Colby) | CHEAL found | value E (according to Colby) |
|---|---|---|---|---|---|
| A1 | 20 | 5% | | 50% | |
| B2.9 | 5 | 5% | | | |
| | 10 | | | 5% | |
| A1 + B2.9 | 20 + 5 | 25% | 10% | | |
| | 20 + 10 | | | 75% | 53% |

B.III

| Compound | Dosage [g ai/ha] | SEBEX found | value E (according to Colby) | PHBPU found | value E (according to Colby) |
|---|---|---|---|---|---|
| A1 | 10 | 0% | | 5% | |
| B2.13 | 2.5 | 30% | | 85% | |
| A1 + B2.13 | 10 + 2.5 | 70% | 30% | 92% | 86% |

Example B.IV

| Compound | Dosage [g ai/ha] | SEBEX found | value E (according to Colby) | PHBPU found | value E (according to Colby) |
|---|---|---|---|---|---|
| A1 | 20 | 25% | | 20% | |
| B4.2 | 20 | 0% | | 0% | |
| A1 + B4.2 | 20 + 20 | 35% | 25% | 40% | 20% |

Example B.V

| Compound | Dosage [g ai/ha] | ECHCG found | value E (according to Colby) | PHBPU found | value E (according to Colby) |
|---|---|---|---|---|---|
| A1 | 20 | 15% | | | |
| | 10 | | | 5% | |
| B7.1 | 200 | 78% | | | |
| | 100 | | | 75% | |
| A1 + B7.1 | 20 + 200 | 93 | 81% | | |
| | 10 + 100 | | | 93% | 76% |

Example B.VI

| Compound | Dosage [g ai/ha] | SEBEX found | SEBEX value E (according to Colby) | PHBPU found | PHBPU value E (according to Colby) |
|---|---|---|---|---|---|
| A1 | 20 | 45% | | | |
|  | 10 | | | 5% | |
| B9.1 | 5 | 0% | | | |
|  | 10 | | | 78% | |
| A1 + B9.1 | 20 + 5 | 70% | 45% | | |
|  | 10 + 10 | | | 90% | 79% |

Example B.VII

| Compound | Dosage [g ai/ha] | ECHCG found | ECHCG value E (according to Colby) | SEBEX found | SEBEX value E (according to Colby) |
|---|---|---|---|---|---|
| A1 | 20 | 15% | | 15% | |
| B10.1 | 50 | 0% | | | |
|  | 100 | | | 5% | |
| A1+ B10.1 | 20 + 50 | 45% | 15% | | |
|  | 20 + 100 | | | 75% | 48% |

Example B.VIII

| Compound | Dosage [g ai/ha] | CYPSE found | CYPSE value E (according to Colby) | CHEAL found | CHEAL value E (according to Colby) |
|---|---|---|---|---|---|
| A1 | 10 | 0% | | | |
|  | 20 | | | 50% | |
| B11.1 | 200 | 10% | | | |
|  | 100 | | | 0% | |
| A1 + B11.1 | 10 + 200 | 25% | 10% | | |
|  | 20 + 100 | | | 75% | 50% |

Example B.IX

| Compound | Dosage [g ai/ha] | SCPJU found | SCPJU value E (according to Colby) | SAGPY found | SAGPY value E (according to Colby) |
|---|---|---|---|---|---|
| A1 | 18 | 50% | | 50% | |
| B1.2 | 187 | 20% | | 0% | |
| A1 + B1.2 | 37.5 + 4.3 | 60% | 60% | 80% | 50% |

Example B.X

| Compound | Dosage [g ai/ha] | SCPJU found | SCPJU value E (according to Colby) | MOOVA found | MOOVA value E (according to Colby) |
|---|---|---|---|---|---|
| A1 | 37.5 | 30% | | | |
|  | 18 | | | 60% | |
| B2.2 | 1.8 | 0% | | 0% | |
| A1 + B2.2 | 37.5 + 1.8 | 50% | 30% | | |
|  | 18 + 1.8 | | | 80% | 60% |

Example B.XI

| Compound | Dosage [g ai/ha] | SCPJU found | SCPJU value E (according to Colby) | SAGPY found | SAGPY value E (according to Colby) |
|---|---|---|---|---|---|
| A1 | 75 | 50% | | | |
|  | 37.5 | | | 70% | |
| B2.5 | 15 | 0% | | | |
|  | 7.5 | | | 0% | |
| A1 + B2.5 | 75 + 15 | 70% | 50% | | |
|  | 37.5 + 7.5 | | | 100% | 70% |

Example B.XII

| Compound | Dosage [g ai/ha] | ECHOR found | ECHOR value E (according to Colby) | CYPSE found | CYPSE value E (according to Colby) |
|---|---|---|---|---|---|
| A1 | 37.5 | 60% | | 20% | |
| B3.1 | 25 | 30% | | | |
|  | 50 | | | 0% | |
| A1 + B3.1 | 37.5 + 25 | 100% | 65% | | |
|  | 37.5 + 50 | | | 40% | 20% |

Example B.XIII

| Compound | Dosage [g ai/ha] | SCPJU found | SCPJU value E (according to Colby) | CYPSE found | CYPSE value E (according to Colby) |
|---|---|---|---|---|---|
| A1 | 37.5 | 30% | | | |
|  | 150 | | | 60% | |
| B4.1 | 22 | 0% | | 0% | |
| A1 + B4.1 | 37.5 + 22 | 50% | 30% | | |
|  | 150 + 22 | | | 90% | 60% |

Example B.XIV

| Compound | Dosage [g ai/ha] | SCPJU found | SCPJU value E (according to Colby) | SAGPY found | SAGPY value E (according to Colby) |
|---|---|---|---|---|---|
| A1 | 37.5 | 50% | | 70% | |
| B5.1 | 125 | 0% | | | |
|  | 63 | | | 0% | |

-continued

| Compound | Dosage [g ai/ha] | SCPJU found | value E (according to Colby) | SAGPY found | value E (according to Colby) |
|---|---|---|---|---|---|
| A1 + B5.1 | 37.5 + 125 | 70% | 50% | | |
| | 37.5 + 63 | | | 100% | 70% |

Example B.XV

| Compound | Dosage [g ai/ha] | SCPJU found | value E (according to Colby) | CYPSE found | value E (according to Colby) |
|---|---|---|---|---|---|
| A1 | 37.5 | 50% | | 20% | |
| B5.2 | 4.3 | 0% | | 0% | |
| A1 + B5.2 | 37.5 + 4.3 | 98% | 50% | 100% | 20% |

Example B.XVI

| Compound | Dosage [g ai/ha] | SCPJU found | value E (according to Colby) | MOOVA found | value E (according to Colby) |
|---|---|---|---|---|---|
| A1 | 18 | 20% | | 60% | |
| B8.1 | 375 | 0% | | | |
| | 187 | | | 0% | |
| A1 + B8.1 | 18 + 375 | 50% | 20% | | |
| | 18 + 187 | | | 90% | 60% |

We claim:

1. A herbicidal composition comprising synergistically effective amount of

A) at least one compound of the formula (I) and agriculturally customary salts thereof [component (A)]

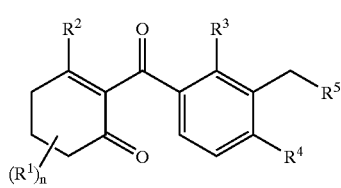

(I)

where $R^1$ is $C_1$–$C_4$-alkyl;
$R^2$ is $OR^6$, $SO_mR^7$, cyanato, cyano, thiocyanato or halogen;
$R^3$ and $R^4$ independently of one another are hydrogen, halogen, $C_1$–$C_4$-alkyl, halogen-$C_1$–$C_4$-alkyl, cyano, nitro or $SO_mR^7$;
$R^5$ is O—$(CH_2)_a$—O—$(CH_2)_b$—$OR^7$, $C_3$–$C_8$-cycloalkyloxy, $C_3$–$C_8$-cycloalkyl-$C_1$–$C_4$-alkyloxy, 2-tetrahydrofuranylmethoxy, 3-tetrahydrofuranylmethoxy, 2-tetrahydro-2H-pyranylmethoxy, 2-tetrahydrothienylmethoxy, 2-furanylmethoxy or 2-thienylmethoxy;
$R^6$ is hydrogen, $C_1$–$C_4$-alkyl or halogen-$C_1$–$C_4$-alkyl;
$R^7$ is $C_1$–$C_4$-alkyl, $C_2$–$C_4$-alkenyl, $C_2$–$C_4$-alkynyl, halogen-$C_1$–$C_4$-alkyl, halogen-$C_2$–$C_4$-alkenyl or halogen-$C_2$–$C_4$-alkynyl;
n is 0, 1, 2, 3, 4, 5 or 6;
m is 0, 1 or 2;
a is 2, 3 or 4;
b is 2, 3 or 4; and B) at least one compound [component (B)] from the group consisting of the herbicides benfuresate, bensulfuron, bispyribac-sodium, clomazone, cyhalofop-butyl, ethoxysulfuron, fenoxaprop-ethyl, N-[(4,6-dimethoxypyrimidin-2-yl)aminocarbonyl]-2-dimethylaminocarbonyl-5-formylaminobenzenesulfonamide (foramsulfuron), glufosinate, glyphosate, halosulfuron-methyl, imazamox, imazapyr, imazaquin, imazethapyr, imazosulfuron, iodosulfuron-methyl-sodium, mefenacet, N-[(4,6-dimethoxypyrimidin-αyl)aminocarbonyl]-α-methoxycarbonyl-5-methylsulfonylaminomethylbenzenesulfonamide (mesosulfuron), metosulam, metsulfuron-methyl, oxadiargyl, oxaziclomefone, pentoxazone, pendimethalin, propanil, quinclorac and thiobencarb, these compositions comprising the compounds of the formula (I) or salts thereof [component (A)] and the compounds of the group B) [component (B)] in a weight ratio of 1:2 000 to 2 000:1.

2. A herbicidal composition as claimed in claim 1, which comprises, as component (A), a compound of the formula (I) where $R^1$ is methyl;
$R^2$ is $OR^6$;
$R^3$ and $R^4$ independently of one another are hydrogen, chlorine, fluorine, methyl, trifluoromethyl, cyano, nitro or $SO_2R^7$;
$R^6$ is hydrogen;
$R^7$ is methyl or ethyl;
n is 0, 1 or 2;
m, a and b are in each case 2.

3. A herbicidal composition as claimed in claim 1, which comprises, as component (A), a compound of the formula I where $R^5$ is O—$(CH_2)_a$—O—$(CH_2)_b$—$OR^7$, $C_3$–$C_8$-cycloalkyloxy, $C_3$–$C_8$-cycloalkyl-$C_1$–$C_4$-alkyloxy or 2-tetrahydrofuranylmethoxy.

4. A herbicidal composition as claimed in claim 1, wherein the weight ratio A:B of the combined herbicides (A) and (B) is in the range of from 1:20 to 20:1.

5. A herbicidal composition as claimed in claim 1, which comprises 0.1–99% by weight of herbicides (A) and (B) and 99 to 0.1% by weight of formulation auxiliaries conventionally used in crop protection.

6. A method of controlling undesired vegetation, which comprises applying one or more herbicides (A) together with one or more herbicides (B) to the harmful plants, plant parts thereof or the area under cultivation, the combination of the herbicides (A) and (B) being as defined in claim 1.

* * * * *